Nov. 8, 1949. C. W. CHAFFIN Plant Pat. 892
CLIMBING ROSE PLANT
Filed Jan. 14, 1948
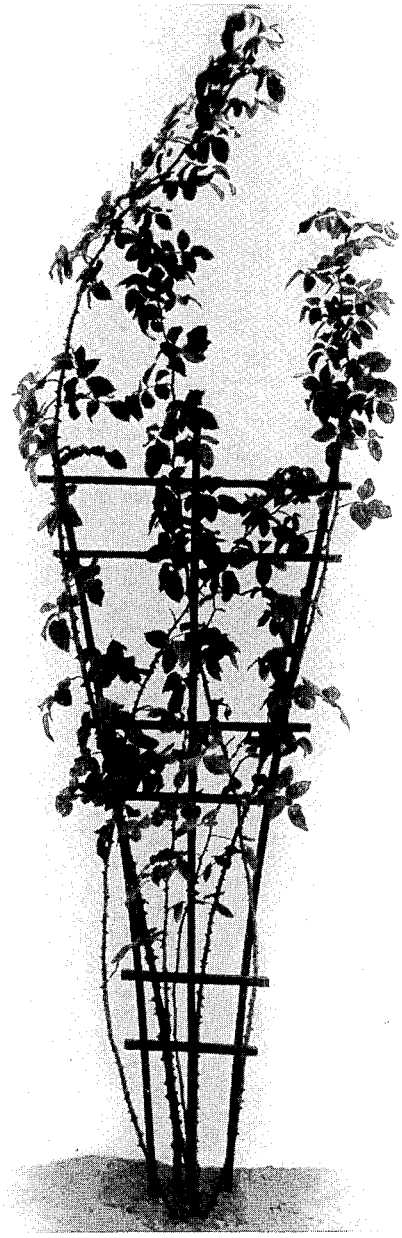
Inventor:
C. W. Chaffin
By Robb & Robb
Attorneys Patented Nov. 8, 1949

Plant Pat. 892

UNITED STATES PATENT OFFICE

892

CLIMBING ROSE PLANT

Carl W. Chaffin, Ontario, Calif., assignor to Armstrong Nurseries, Inc., Ontario, Calif., a corporation of California Application January 14, 1948, Serial No. 2,252

1 Claim. (Cl. 47—61)

The present discovery relates to a new and distinct variety of climbing hybrid tea rose plant, originating as a bud sport which I found growing on a bush rose of the variety "Show Girl" (Pl. Pat. #646), in the nursery row at Ontario, California.

This new variety, comparing it with its parent, is characterized as to novelty, predominantly, by its vigorous climbing habit, the season of bloom and the manner in which the blooms are produced, and is distinct from all other climbing hybrid tea varieties, as well as all other climbing varieties, so far as I know, in the combination of color, form, and size of the flowers, substantially as specifically described in prior Plant Patent No. 646, dated October 24, 1944, and as illustrated therein.

Whereas the bush rose "Show Girl" produces flowers on stems originating as laterals from relatively short main canes and side branches from these main canes, this new variety produces flowers on lateral-growing stems from long canes measuring as much as twelve to fifteen feet in length. As is typical of most climbing hybrid tea varieties originating as sports from bush rose types, this new variety produces the major portion of its flowers in the spring (usually in April and May) with fewer scattered flowers throughout the remainder of the growing season. Because of these traits, this new variety is suitable for planting adjacent to and covering walls, fences, pergolas, etc., for which the bush rose variety is unsuited.

Asexual reproduction shows that the characteristics hold true through succeeding propagations.

The accompanying drawing illustrates a specimen of this new variety, depicting its climbing habit to a height much beyond that of a six-foot trellis, and the manner in which foliage is produced.

The following is a detailed description of the new variety, all references to color being in accordance with the R. F. Wilson's Horticultural Colour Chart, except where indicated to be in accordance with Ridgway's Color Standards and Nomenclature:

Type: Tall; climbing.
Class: Climbing hybrid tea.
Discovery: Sport.
*Parent.*—"Show Girl" (Pl. Pat. No. 646).
Propagation: Holds its distinguishing characteristics through succeeding propagations by budding, the only method tried so far.

*Flower*

Locality where grown: Ontario, California.
Flowers borne: Singly and at times several to stem; in irregular cluster; on normal, medium long stems.
Quantity of bloom: Free; outdoors, Continuity: Principally one season of bloom in the spring.
Fragrance: Moderate; tea.
Bud:
*Peduncle.*—Medium length; medium caliper; erect; medium rough; few gland-tipped cilia; on some pedicels a few hairs. *Color*—near Fern Green, Plate 0862/1, page 186.
*Before calyx breaks—Size*—medium. *Form*—short, pointed, without a conspicuous neck; with or without foliaceous appendages, tomentum, gland-tipped cilia on the surface of the bud; often with slender, much cut, bristle-like foliaceous parts extending beyond the tip of the bud equal to one-fourth or more of its length.
*As calyx breaks.*—Near Rose Madder, Plate 23, page 23. *Sepals*—inner surface with fine, woolly tomentum on margins of alternate sepals, lined with stipitate and sessile glands.
*As first petals open.—Size*—medium. Petal does not fold back to any extent until the bud has reached maturity though petals all loosen considerably from the initial tightly clasping state. *Form*—short; ovoid to globular. *Color*—outside: near Crimson, Plate 22, page 22; inside: Crimson, Plate 22, page 22, and gradually passing into near Crimson, Plate 22/2, page 22.
*Opening.*—Opens up well.
Bloom: Size, when fully open—medium to large; four inches to five inches.
*Petalage.*—Semi-double (two or even three regularly; three to five petaloids arranged irregularly.
*Form.*—Cupped to high center at first; becoming open to cupped: petals at first tightly flat; becoming later, at maturity, loosely flat to cupped or rolled outward.
Petals: Thick, with inside satiny and outside shiny.
*Shape.*—Outside: round, obovate, mucronate; sometimes scalloped apex with one or two occasional notches. The center row of petals on some blooms are more scalloped than others. Intermediate: obovate, murconate; scalloped at times with one or two notches. Inside: obovate; mucronate; scalloped seldom, irregular apex. On the petaloids of some blooms is a distinct vegetative ridge running from base to apex, off center, and often a light shade.
*Color.*—Colors may be modified by being pencilled and shaded with other colors.

This description of a newly opened flower was made from a rose grown outdoors and allowed to open three days indoors, in the month of August, at Ontario, California. This description of petals was made from a rose grown in sandy soil:

*Color.—Outside petal*—outside surface: near Phlox Pink, Plate 625, page 77, then toward apex near Phlox Pink, Plate 625/1, page 77; inside surface: near Phlox Pink, Plate 625, page 77, then to edge near apex, Phlox Pink, Plate 625/1, page 77, at base of petal near Aureolin, Plate 3/2, page 3. *Intermediate petal*—outside surface: this row of petals usually an even tone of near Phlox Pink, Plate 625, page 77, on the outside and inside surfaces. At base of petal near Aureolin, Plate 3/2, page 3. *Inner petal*—outside surface: near Rose Madder, Plate 23/1, page 23; inside surface: near Rose Madder, Plate 23, page 23, with more near Aureolin, Plate 3/2, page 3, showing at base.

This description was made from a rose that was open for three days outdoors in the month of August, at Ontario, California:

*Color.—Outside petal*—outside surface: near Phlox Pink, Plate 625/1, page 77, to near Phlox Pink, Plate 625/2, page 77, toward apex; inside surface: very little difference from outside surface except occasionally, because of more exposure to sun, the color may be a trifle lighter. This would be then between Phlox Pink, Plate 625/1, page 77, and Phlox Pink, Plate 625/3, page 77. *Inside petal*—outside surface: Even hue of near Phlox Pink, Plate 625/1, page 77; inside surface: Similar to outside surface or, near Phlox Pink, Plate 625/1, page 77, with a very narrow margin at top of petal of near Phlox Pink, Plate 625/3, page 77. Pencilling is quite pronounced on nearly all petals. Outdoors they become yellowish white about ¼″ to ¾″ from base when blooms are almost finished.

*General color effect.*—Newly opened flower—all petals showing about an even tone in coloring near Phlox Pink, Plate 625, page 77. Three days open—near Phlox Pink, Plate 625/1, page 77.

*Behavior.*—Drop off cleanly but sometimes a few petaloids will cling to receptacle. When checked, flowers and color not materially affected by hot dry weather except some diminished size.

*Flower longevity.*—On climber in garden—3 to 4 days in August. Cut roses grown outdoors kept at living room temperatures—3 days in August.

*Reproductive organs*

Stamens: Medium number; arranged regularly about pistils, mixed with petaloids sometimes.
Filaments: Medium to long.
Anthers: Medium size; open at various times. *Color*—near Orpiment Orange, Plate 10/2, page 10, to near Jasper Red, Plate 018, page 107.
Pollen: Near Chinese Yellow, Plate 606, page 68.
Pistils: Medium number.
Styles: Even; medium length; medium caliper; bunched.
Stigma: *Color*—near Chrysanthemum Crimson, Plate 824/2, page 169.
Ovaries: Some protruding from calyx.
Hips: Short; globular with inconspicuous neck.

*Color*—near Citron Green, Plate 763/2, page 100, and blotched with near Indian Lake, Plate 826/2, page 170. Hips seldom formed on the plants.
Sepals: Permanent; moderately short. *Color*—inside: near Erythrite Red, Plate 0027/1, page 190; outside: near Scheeles Green, Plate 860, page 175.
Seeds: Few; medium size.

*Plant*

Foliage:
*Leaves.*—Compound of seven leaflets; normally abundant; medium to large; heavy; leathery.
*Leaflets.—Shape*—ovate with apex usually acute, sometimes quite obtuse; base round; margin simply serrate.
*Color.—Mature*—upper surface: near Spinach Green, Plate 0960, page 187; under surface—between Rainette Green, Plate XXXI (Ridgway) and Absinthe Green, Plate XXXI (Ridgway). *Young*—upper surface: Lettuce Green, Plate 861, page 176, overlaid with Oxblood Red, Plate 00823, page 191; under surface: Pea Green, Plate 61/2, page 61, overlaid with Oxblood Red, Plate 00823, page 191.
*Rachis.*—Medium heavy. Upper side—grooved; glandular; under side—smooth with occasional small thorns.
*Stipules.*—Average length; average width; medium long points, turning out at an angle of slightly more than 45°.
*Disease.*—Resistant to mildew.

Growth:
*Habit.*—Climbing.
*Growth.*—Vigorous.
*Canes.*—Heavy.
*Main stems.*—Near Lettuce Green, Plate 861, page 176. *Large prickles*—several; medium to long; hooked downward; with short narrow base. Color—mostly Ochraceous Tawny, Plate XV (Ridgway) and some Deep Colonial Buff, Plate XXX (Ridgway). *Small prickles* — none. *Hairs*—none.
*Branches.*—Near Lettuce Green, Plate 861, page 176. *Large prickles*—several; medium long; hooked downward; with narrow base. Color—deep Colonial Buff, Plate XXX (Ridgway), and where exposed to sun, Ochraceous Tawny, Plate XV (Ridgway). *Small prickles*—few. *Hairs*—none.
*New shoots.*—Near Lettuce Green, Plate 861/3, page 176, overlaid with Oxblood Red, Plate 00823, page 191. *Large prickles*—few; medium long; straight to hooked downward; with narrow base. Color—near Pea Green, Plate 61/1 page 61, overlaid with Oxblood Red, Plate 00823, page 191. *Small prickles*—few. *Hairs*—none.

I claim:

A new and distinct variety of rose plant, characterized as to novelty by its vigorous climbing habit, in combination with the season of bloom and the manner in which its blooms are produced, substantially as shown and described.

CARL W. CHAFFIN.

No references cited.